(12) United States Patent
Lomask et al.

(10) Patent No.: US 7,402,137 B2
(45) Date of Patent: Jul. 22, 2008

(54) ADJUSTABLE TABLE PLETHYSMOGRAPH

(75) Inventors: Joseph Lomask, Wilmington, NC (US); Steve Karpinski, Wilmington, NC (US)

(73) Assignee: Buxco Electronics, Inc., Sharon, CT (US)

( * ) Notice: Subject to any disclaimer, the term of this patent is extended or adjusted under 35 U.S.C. 154(b) by 469 days.

(21) Appl. No.: 10/838,392

(22) Filed: May 4, 2004

(65) Prior Publication Data
US 2005/0251053 A1 Nov. 10, 2005

(51) Int. Cl.
*A61B 5/02* (2006.01)
(52) U.S. Cl. .................... 600/504; 600/21; 128/202.12; 128/205.26
(58) Field of Classification Search .............. 5/607, 5/608; 312/349, 334.1, 330.1, 281, 282; 312/284; 108/143, 33, 38; 600/21, 504, 600/531; 128/202.12, 205.26; 220/345.1, 220/345.2; 206/372–379
See application file for complete search history.

(56) References Cited

U.S. PATENT DOCUMENTS

| | | | | |
|---|---|---|---|---|
| 859,454 A * | 7/1907 | Larsson | ...................... | 108/134 |
| 2,508,846 A * | 5/1950 | Wallin | ...................... | 601/43 |
| 2,569,849 A * | 10/1951 | Emerson | ...................... | 600/541 |
| 4,402,315 A | 9/1983 | Tsuda et al. | | |
| 4,622,852 A | 11/1986 | James et al. | | |
| 4,727,870 A * | 3/1988 | Krasle | ...................... | 128/202.12 |
| 5,308,310 A * | 5/1994 | Roff et al. | ...................... | 600/21 |
| 5,379,777 A * | 1/1995 | Lomask | ...................... | 600/529 |
| 5,379,778 A * | 1/1995 | Century | ...................... | 600/531 |
| 5,398,694 A | 3/1995 | Poppendiek et al. | | |
| 5,438,939 A * | 8/1995 | Clarke | ...................... | 108/147 |
| 5,980,463 A | 11/1999 | Brockway et al. | | |
| 6,015,388 A | 1/2000 | Sackener et al. | | |
| 6,059,732 A | 5/2000 | Orr et al. | | |
| 6,101,956 A * | 8/2000 | Keil | ...................... | 108/147 |
| 6,113,550 A * | 9/2000 | Wilson | ...................... | 600/534 |
| 6,287,264 B1 | 9/2001 | Hoffman | | |
| 6,299,582 B1 | 10/2001 | Brockway et al. | | |
| 6,350,242 B1 | 2/2002 | Doten et al. | | |
| 6,475,157 B2 * | 11/2002 | Wilson | ...................... | 600/529 |
| 6,506,161 B2 | 1/2003 | Brockway et al. | | |
| 6,702,764 B2 * | 3/2004 | Dempster et al. | ........... | 600/587 |
| 2003/0125643 A1 * | 7/2003 | Dempster et al. | ........... | 600/587 |

FOREIGN PATENT DOCUMENTS

| | | |
|---|---|---|
| DE | 2812447 A1 | 9/1979 |
| WO | WO 92/18084 | 10/1992 |

* cited by examiner

*Primary Examiner*—Robert L. Nasser, Jr.
*Assistant Examiner*—Karen E Toth
(74) *Attorney, Agent, or Firm*—MacCord Mason PLLC

(57) ABSTRACT

A plethysmograph is constructed with a base including parallel, horizontal guide rails; an open-ended, moveable enclosure section having a horizontal central axis slidable on the guide rails between open and closed positions; a fixed enclosure section mounted on the base transverse to the horizontal pathway, the fixed enclosure section including an inner face toward the open end of the enclosure section adapted for sealing engagement with the open end of the moveable enclosure section when the moveable enclosure section is in its closed position; and a support table attached to the fixed section, the table projecting into the moveable enclosure section when the moveable enclosure section is in the closed position, the table being vertically adjustable and having an angularly adjustable longitudinal axis.

8 Claims, 2 Drawing Sheets

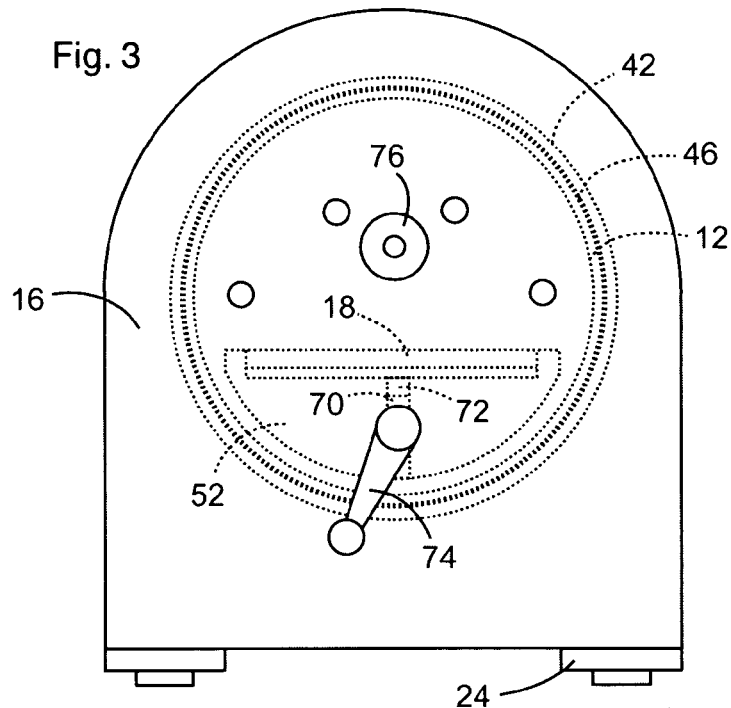
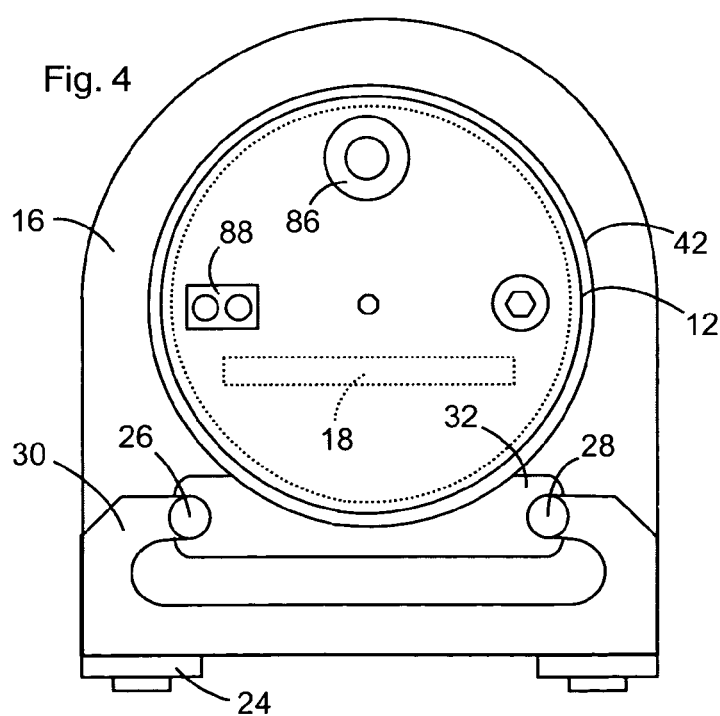
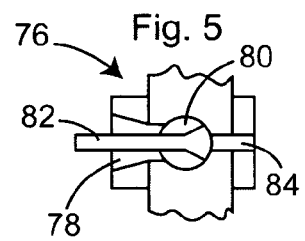
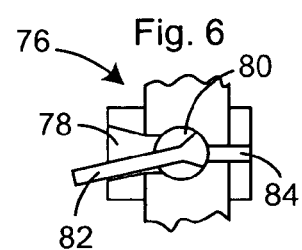
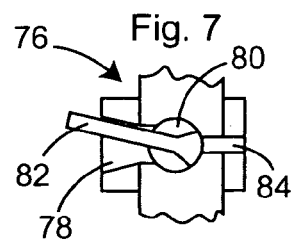

ADJUSTABLE TABLE PLETHYSMOGRAPH

BACKGROUND OF THE INVENTION (1) Field of the Invention

The present invention relates to plethysmographs used to measure changes in air volume, such as in pulmonary testing of small animals, and in particular to plethysmographs facilitating accurate positioning of anesthetized animals for tracheal cannula insertion during laboratory testing.

(2) Description of the Prior Art

Various laboratory procedures require an analysis of the respiratory patterns of small test animals. Respiratory data is collected by enclosing the animal in the chamber of a device known as a plethysmograph, and measuring changes in air pressure within the chamber during the test procedure.

A plethysmograph is generally comprised of an enclosure with a closeable access opening to permit placement and removal of the test animal, and a cover to releasibly fit over the enclosure access opening. The enclosure is provided with a means for controlled air access and egress, a means to measure variations in air pressure within the enclosure, such as a differential pressure transducer, and commonly a means for administering test materials to the animal during the test procedure.

Test animals may be anesthetized and tracheotomized during many test procedures. Therefore, plethysmographs often include a table to support the animal. Usually, the table will include a horizontal upper surface upon which the animal is placed, normally on its back, with the animal's head toward the end or side of the chamber through which the tracheal cannula is inserted during the test procedure.

To facilitate opening and closing, one section of the enclosure, either the open-ended chamber or the cover, may be held in a stationary position, while the other section is moveable between an open position and a closed position. In the closed position, the open end of the chamber releasibly engages the cover in a sealing fashion to prevent air from entering the chamber between the two sections. For example, as taught in U.S. Pat. No. 5,379,778, an air-tight seal may be achieved by positioning an O-ring between the chamber opening and the cover.

Prior art plethysmographs are less than optimal. First, due to variations in animal sizes, accurate placement of the tracheal cannula is not always possible. Second, fitting of the chamber cover onto the chamber may be difficult due to the need to align the chamber opening with the corresponding connection area of the cover. Therefore, there is a need for further improvements in prior art plethysmographs.

SUMMARY OF THE INVENTION

The present invention is directed to plethysmographs of the type used to contain laboratory animals during laboratory testing, such as in the collection of pulmonary data. The devices are particularly adapted to accurately position anesthetized animals, such as mice, hamsters and rats, so that the tracheal cannula can be correctly inserted. In addition, the plethysmographs of the present invention enable quick and accurate joinder of the enclosure sections.

The present plethysmographs are similar to the prior art plethysmographs described above in that the present plethysmographs are comprised of a stationary support base, a fixed enclosure section with an inner face mounted on the base, and a moveable enclosure section with an open inner end that is moveable horizontally between an open position and a closed position. In the closed position, the inner end of the moveable enclosure fits in sealing engagement with the inner face of the fixed enclosure section. An animal support table is mounted on the inner face of the fixed enclosure section, and projects into the moveable enclosure section when the moveable enclosure section is in the closed position.

The plethysmograph of the present invention incorporates at least one, and preferably all three of the following improvements. First, the current device provides means for adjusting the angle of the table relative to horizontal, enabling more accurate insertion of tracheal cannula into the anesthetized animal. Second, the table can be vertically adjusted up or down, providing either further adjustability and greater accuracy in tracheal cannula placement. Third, the moveable enclosure section of the present device is supported on guide rails, facilitating accurate alignment of the mouth or open end of the moveable section with the receiving area of the fixed section inner face, thereby enabling rapid and accurate positioning and sealing of the two sections.

More specifically, the plethysmographs of the present invention are comprised of an open-ended chamber to enclose the test animal, a base, a chamber cover mounted on a stationary base to mate with the open end of the chamber to form an airtight enclosure, and a table mounted on the cover and projecting into the chamber. In the preferred embodiment, the chamber or first enclosure section is in the shape of an elongated cylinder having a horizontal central axis. It will be apparent, however, that chambers of different configurations are within the scope of the invention, so long as the chambers are moveable along a horizontal pathway and have a mouth or open end dimensioned to mate with a part of the closure or cover to form an airtight seal.

The base upon which the cover is mounted includes horizontal guide rails and the chamber includes guides slidably engaging the rails so that the chamber is slidable on the rails between an open position, which may be on the rails, or completely detached from the base, and a closed position in which the chamber opening forms an airtight seal with the cover.

In order to provide an airtight seal, the cover may include a continuous wall dimensioned to fit with the interior or exterior of the open end of the chamber. For example, as described in the detailed description, the cover may include an inwardly projecting annular ring with a continuous inner wall dimensioned to correspond to the exterior dimension of the chamber at the chamber opening. Alternatively, the projection may be a boss with exterior dimensions corresponding to the interior dimensions of the chamber at the chamber opening. Other configurations will also be apparent. For example, an annular groove may be cut into the inner face of the cover, with the groove being dimensioned to receive the open end of the chamber, and the inner or outer side of the groove forming a wall to engage the chamber open end. An O-ring may be positioned between the chamber open end and the cover receiving wall to provide an airtight seal between chamber and cover.

The cover wall and chamber mouth are parallel and aligned when the chamber is slidably mounted on the base. Therefore, as the chamber is moved to the closed position, chamber open end will accurately mate with the cover receiving wall.

Unlike stationary tables described in the prior art, the table of the present plethysmograph is attached by horizontal hinge to a table mount on the fixed cover. In addition, the table mount is vertically positionable. Therefore, unlike prior art fixed tables, the table of the present invention can be raised or lowered and tilted up or down relative to a fixed cannula port, normally mounted on and extending through the cover. As a result, more accurate alignment of the cannula with the test animal is achievable.

In operation, the chamber is opened, and the angle and height of the table is adjusted relative to the cannula port to conform to the size of the test animal. The anesthetized test animal is then positioned on the table and a cannula is inserted. The chamber is then slid along the rails until the chamber opening mates with the cover wall, forming an airtight seal. During testing, pulmonary measurements are made using a differential pressure transducer.

BRIEF DESCRIPTION OF THE DRAWINGS

FIG. 3 is an end view of one end of the plethysmograph.

FIG. 4 is an end view of the other end of the plethysmograph.

FIG. 5 is a detailed sectional side view of the tracheal port with the tracheal conduit in the horizontal position.

FIG. 6 is a detailed sectional side view of the tracheal port with the tracheal conduit in the lowered position.

FIG. 7 is a detailed sectional side view of the tracheal port with the tracheal conduit in the raised position.

DETAILED DESCRIPTION OF THE INVENTION

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

The preferred embodiment of the invention incorporates the three improvements over prior art devices described above. Specifically, the preferred plethysmograph comprising a) a base including a platform and parallel, horizontal guide rails above the platform; b) a moveable enclosure section having a horizontal central axis parallel to the guide rails, a closed outer end and an open inner end perpendicular to the central axis, the enclosure section being slidable on the guide rails between open and closed positions; c) a fixed enclosure section mounted on the platform transverse to the horizontal pathway, the fixed enclosure section including an inner face toward the open end of the enclosure section, the inner face being adapted for sealing engagement with the open end of the moveable enclosure section when the moveable enclosure section is in its closed position; and d) a support table attached to the fixed section, the table extending into the moveable enclosure section when the moveable enclosure section is in the closed position, the table being vertically adjustable and having a longitudinal axis angularly adjustable relative to horizontal.

Figure 1:
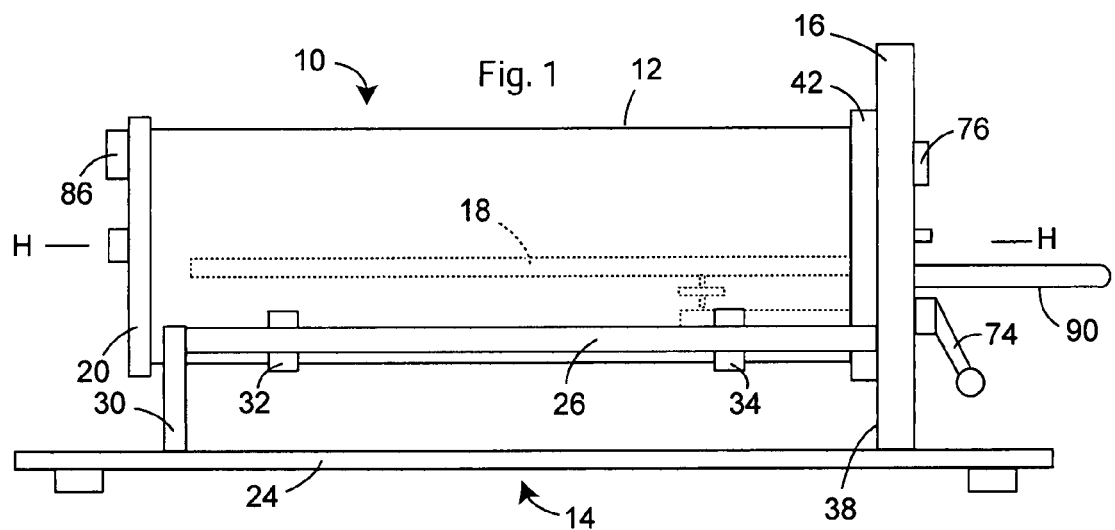
FIG. 1 is a side view of the preferred embodiment plethysmograph.
Figure 2:
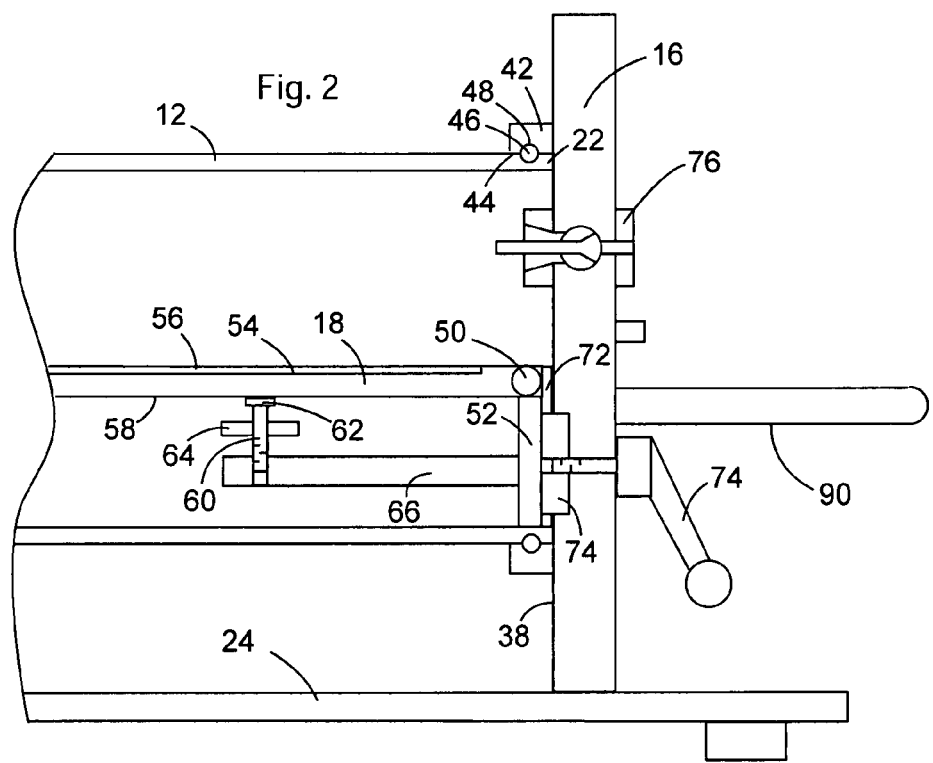
FIG. 2 is a sectional side view of a part of the plethysmograph.

As best shown in FIG. 1, plethysmograph, generally 10, is comprised of a chamber or first enclosure section 12, a stationary base 14, a cover or second enclosure section 16 attached to base 14, and table 18 projecting inwardly from section 16 into the interior of section 12. First enclosure section 12 has a closed end 20 and an open end 22. In the preferred embodiment, enclosure section 12 is in the shape of an elongated cylinder having a horizontal central axis H, with ends 20 and 22 being perpendicular to the axis H.

Stationary base 14 is comprised of a footed platform 24 and first and second parallel, horizontal guide rails 26 and 28 mounted above platform 24 between mount 30 adjacent a first end of platform 24 and second enclosure section 16. First enclosure section 12 includes spaced guides 32 and 34 slidably mounted on rails 26 and 28. As shown in the preferred embodiment, rails 26 and 28 have circular cross-sections, and guides 32 and 34 each have opposed ends with semi-circular cutouts that slide along rails 26 and 28. Rails 26 and 28 are parallel to the central axis H while guides 32 and 34 are transverse to central axis H.

Second enclosure section 16 is mounted on, and extends vertically upward from, a second end of platform 24. Section 16 includes an inner face 38 that is transverse to the horizontal axis of section 12, and an outer face 40 opposite face 38.

An annular ring 42 projects inwardly from inner face 38. Ring 42 includes a continuous inner surface 44. Axis H extends through the center of ring 42. The diameter of inner surface 44 is approximately equal to the outer diameter of first enclosure section 12. O-ring 46 is positioned within an annular groove 48 adjacent open end 22 of section 12 at a distance from the edge of section 12 less than the thickness of surface 44, providing an air-tight seal between sections 12 and 14 when end 22 is fully inserted onto ring 42.

Table 18 is attached by horizontal hinge 50 to table mount 52, which in turn is releasibly attached to inner face 38 of section 16 within the circumference of annular ring 42. Table 18 includes an upper surface 54 with a raised outer edge 56, and a lower surface 58. The angle between the longitudinal axis of table 18 relative to axis H is adjusted with vertically extendable set screw 60 that includes an upper end cap 62 to engage table lower surface 58. Knurled wheel 64 attached to screw 60 facilitates manual rotation of screw 60 within a threaded bore in mounting plate 64 that extends inwardly from mount 52 beneath table 18. Rotation or counter-rotation of screw 60 by wheel 64 vertically extends or retracts cap 62, as the case may be, thereby changing the angle of the longitudinal axis of table 18 relative to axis H. Generally, the angle of table 18 may be adjusted above or below horizontal by up to about ±10° relative to horizontal.

Table mount 52 is also vertically adjustable, permitting even greater accuracy in placement of the cannula. As shown in the preferred embodiment, clamp 70 carried in groove 72 of mount 52, is moveable horizontally by rotation of clamping arm 74 to frictionally clamp table mount 52 when in the tightened clamping position and releases mount 52, and thereby table 18 for movement up or down relative to section 12 and 16 when in the loosened or release position.

Plethysmograph 10 further includes a cannula or tracheal port 76 vertically aligned above axis H, through which a trachea, not shown, is inserted. As illustrated in detail in FIGS. 5-7, port 76 is comprised of a socket 78 having a conical outlet on its inner side. Ball 80 is rotatable fitted within socket 78 and includes conduit 82 extending inwardly through the conical outlet of socket 78 into the interior of the chamber. An outer conduit 84 extends from the exterior of the chamber to communicate through ball 80 to conduit 82. Ball 80 is rotatable to position conduit 82 approximately 15° above or below horizontal, thereby permitting alignment of the trachea upon upward or downward adjustment of table 18.

Plethysmograph 10 also includes a pneumotach 86, and a differential pressure transducer connection 88. A horizontal support post 90 may extend outwardly from the outer face of section 16 for use in mounting an aerosol block for use in delivering substances using a nebulizer. Other components common to plethysmographs may also be included.

In operation, section 12 is moved horizontally to its open position, or entirely withdrawn from rails 26 and 28. Table 18 is then adjusted to accommodate the size of the test animal by rotating knob 64 to adjust the angle of the longitudinal axis of table 18 relative to horizontal and/or loosening clamp 70 and sliding table 18 up or down as desired. The anesthetized test animal is then positioned on table 18 and a cannula from cannulas port is inserted into the animal.

Section 12 is then moved along rails 26 and 28 to a closed position in which end 22 of section 12 is fully inserted into annular ring 42 to form an airtight seal. The procedure is then initiated.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A plethysmograph enclosure comprising:
   a) a base including a platform and parallel, horizontal guide rails above said platform;
   b) a moveable enclosure section having a horizontal central axis parallel to said guide rails, a closed outer end and an open inner end perpendicular to the central axis, said enclosure section being slidable on said guide rails between open and closed positions;
   c) a fixed enclosure section mounted on said platform transverse to said horizontal pathway, said fixed enclosure section including an inner face toward said open end of said enclosure section and a tracheal port having an inner conduit rotatable above or below horizontal, said inner face being adapted for sealing engagement with the open end of said moveable enclosure section when said moveable enclosure section is in its closed position; and
   d) a support table attached to said fixed section, said table projecting into said moveable enclosure section when said moveable enclosure section is in the closed position, said table being vertically adjustable relative to said tracheal port and having a longitudinal axis angularly adjustable relative to horizontal and to said tracheal port conduit.

2. The plethysmograph enclosure of claim 1, further including a table mount vertically positionable on the inner face of said fixed section, said table being attached by a horizontal hinge to said table mount.

3. The plethysmograph enclosure of claim 1, wherein said table is adjustable up to about ±10° relative to horizontal.

4. The plethysmograph enclosure of claim 1, wherein said table includes a lower surface, said plethysmograph further including a vertically adjustable post having an upper end engaging the lower surface of said table, whereby vertical adjustment of said post changes the angle of said table relative to horizontal.

5. A plethysmograph enclosure comprising:
   a) a moveable enclosure section with an open end;
   b) a fixed enclosure section including an inner face toward said open end of said enclosure section, said inner face being adapted for sealing engagement with the open end of said moveable enclosure section;
   c) a support table attached to said fixed section, said table projecting into said moveable enclosure section when said moveable enclosure section is in the closed position, said table being vertically adjustable; and
   d) an adjustable tracheal port extending through said fixed enclosure section, said port having an inner conduit moveable between a raised position and a lowered position, a ball socket, and an outer conduit extending from the exterior of said fixed enclosure section into said socket, said inner conduit extending from said socket into said movable enclosure, whereby said conduit is alignable with said support table when said table is adjusted to different vertical positions.

6. The plethysmograph enclosure of claim 5, wherein said table has a longitudinal axis that is angularly adjustable relative to horizontal.

7. A plethysmograph enclosure comprising:
   a) a moveable enclosure section with an open end;
   b) a fixed enclosure section including an inner face toward said open end of said enclosure section, said inner face being adapted for sealing engagement with the open end of said moveable enclosure section;
   c) a support table attached to said fixed section, said table projecting into said moveable enclosure section when said moveable enclosure section is in the closed position, said table being vertically adjustable;
   d) a base, said moveable enclosure section being supported on said base and movable along a horizontal pathway; and
   e) an adjustable tracheal port extending through said fixed enclosure section, said port having an inner conduit moveable between a raised position and a lowered position and rotatable above or below horizontal, whereby said conduit is alignable with said support table when said table is adjusted to different vertical positions, said supportable being angularly and vertically adjustable relative to said tracheal port conduit.

8. A plethysmograph enclosure comprising:
   a) a moveable enclosure section with an open end;
   b) a fixed enclosure section including an inner face toward said open end of said enclosure section, said inner face being adapted for sealing engagement with the open end of said moveable enclosure section;
   c) a support table attached to said fixed section, said table projecting into said moveable enclosure section when said moveable enclosure section is in the closed position, said table being vertically adjustable; and
   d) an adjustable tracheal port extending through said fixed enclosure section, said port having an inner conduit moveable between a raised position and a lowered position and rotatable up to about 15° above or below horizontal, whereby said conduit is alignable with said support table when said table is adjusted to different vertical positions.

\* \* \* \* \*